United States Patent [19]

Taylor et al.

[11] 4,253,027
[45] Feb. 24, 1981

[54] TOMOGRAPHIC SCANNER

[75] Inventors: Samuel K. Taylor, Chardon; Joseph W. Erker, Aurora; Robert L. Carper, Hudson, all of Ohio

[73] Assignee: Ohio-Nuclear, Inc., Solon, Ohio

[21] Appl. No.: 915,316

[22] Filed: Jun. 14, 1978

[51] Int. Cl.³ .................. A61B 6/00; H02G 11/00
[52] U.S. Cl. ...................... 250/445 T; 191/12 C
[58] Field of Search .................. 250/445 T; 191/12 C

[56] References Cited

U.S. PATENT DOCUMENTS

| | | |
|---|---|---|
| 3,541,334 | 11/1970 | Sobolewski . |
| 3,852,611 | 12/1974 | Cesar ........................ 250/445 T |
| 3,922,552 | 11/1975 | Tedley ....................... 250/445 T |
| 3,924,131 | 12/1975 | Hounsfield ................. 250/445 T |
| 3,946,234 | 3/1976 | Hounsfield ................. 250/445 T |
| 3,986,031 | 10/1976 | Chekroun ................... 250/445 T |
| 3,999,073 | 12/1976 | Hounsfield et al. ........ 250/445 T |
| 4,001,593 | 1/1977 | Wing et al. ................. 250/522 |
| 4,039,807 | 8/1977 | Bull ........................... 250/445 T |
| 4,063,104 | 12/1977 | Godd .......................... 250/445 T |
| 4,112,303 | 9/1978 | Brandt ........................ 250/445 T |
| 4,114,040 | 9/1978 | Hounsfield ................. 250/445 T |
| 4,114,043 | 9/1978 | Gansfried ................... 250/445 T |
| 4,138,611 | 2/1979 | Hounsfield ................. 250/445 T |

OTHER PUBLICATIONS

Brochure for Catrac Rolling Conductor Carrier, Gemco Electric, pp. 285, 286, 288.
*IEEE Standard Dictionary of Electrical and Electronics Terms*, Wiley-Interscience, 1972, p. 602.

*Primary Examiner*—Alfred E. Smith
*Assistant Examiner*—T. N. Grigsby
*Attorney, Agent, or Firm*—Fay & Sharpe

[57] ABSTRACT

A tomographic scanner for subjecting a planar region of a patient to radiation and producing an image representing the planar region in which at least the source or beam of radiation is moved with a varying speed. In particular, in a traverse and rotate type scanner, a carriage carrying the radiation source and detector(s) is traversed relative to the patient with generally simple harmonic motion. Additionally, vibration is reduced by using a motor, which may include a flywheel, running at substantially constant speed to traverse the carriage. Vibration is further reduced by connecting the motor for rotating the carriage to the carriage through a flexible, e.g. chain, drive. Cable connections to the X-ray tube and other elements carried by the moveable carriage are simplified with a bicycle-chain like flexible cable support.

36 Claims, 5 Drawing Figures

TOMOGRAPHIC SCANNER

BACKGROUND OF THE INVENTION

This application pertains to computerized axial tomographic scanners and more particularly to traverse and rotate type scanners. Traverse and rotate type computerized axial tomographic scanners are well-known in the art, see for example U.S. Pat. No. 3,919,552. Also well-known in the art are the electronics and mathematics for translating the radiation attenuation through the object scanned into a visual representation of the cross section of the object scanned. See for example "The Fourier Reconstruction of a Head Section", Shepp and Logan, IEEE Transaction on Nuclear Science, June, 1974.

In a traditional traverse and rotate system, a beam of radiation and a receiving detector were scanned linearly at a constant speed across a patient in a scan circle during which time attenuation data was taken. After scanning the patient, the radiation source and detector were slowed to a stop in an area outside of the scan circle. The carriage carrying the source and detector were subsequently rotated a few degrees, and accelerated to the desired linear scan speed before reaching the scan circle. A further set of attenuation data was taken as the radiation source/detector traversed the patient in a generally opposite direction but shifted by the few degrees the carriage was rotated. This traverse, then rotate procedure was often repeated on the order of 15 to 180 times to obtain one set of data.

In the past it was commonly believed that the carriage supporting the radiation source and detector system must be traversed at a constant speed. It was believed that nonconstant traverse speeds would produce irregularities in the transmitted attenuation data. As a result only drives for the carriage were used which produced constant speeds when traversing the scan circle. Constant speed drives of the type required are complex and expensive. Because the scan velocity was constant through the scan circle all acceleration and deceleration had to occur outside of the area. The time and space required for realistic changes in speed added to the size and cost of the machine and increased the scan times.

In order to minimize the amount of human organ movement during scans, faster scan times were desired. As a result shorter acceleration and deceleration times were necessary. However, the more sudden were the changes in speed, the greater were the undesirable forces on the scanner parts. Additional wear, vibration and maintenance occured as a partial result of increased forces due to shorter acceleration and deceleration times.

To achieve the linear speed across the patient with rapid slowing and acceleration and deceleration at the extremes of the traverse, nonlinear gear boxes were often used. Ball screw drives were also used to drive the source and detector carriage through the rapidly changing speeds. Both these mechanical gearings were sometimes a source of undesirable vibration in the system.

SUMMARY OF THE INVENTION

The present invention contemplates new and improved traverse and rotate scanning apparatus which overcomes all of the above referred problems and provides a scanner which is fast, simple, inexpensive, and produces high resolution.

In accordance with the present invention, a traverse and rotate scanner is provided in which the source of radiation and the detectors are traversed on a carriage at a nonlinear speed. Data samplings are taken at spacially controlled increments rather than time controlled increments.

In accordance with a more limited aspect of the invention, a continuously operated drive mechanism is used which accelerates and decelerates the source and detector carriage over the entire distance traversed.

In accordance with another aspect of the invention, a vibration insulating drive such as a flexible drive is used in producing rotational indexing between traverses.

In accordance with yet another aspect a flexible linkage with two degrees of freedom supports electrical cable connections to electrical components mounted on the carriages.

One advantage of the present system is the smoothness of operation. The source and detector carriage accelerates and decelerates gradually over the entire scan length. This more gradual change decreases the time and distance of traverse, thus increasing the scan speed. Smaller forces accompany the more gradual acceleration and deceleration, thus reducing or eliminating many sources of vibration.

Another advantage of the present invention is that it uses relatively small power sources to create the smaller forces. The use of smaller motors reduces cost, wear and stress.

A further advantage of the present invention is the high degree of resolution. Spacial samplings of the radiation detector may be taken at intervals of one millimeter or less. The sampling positions being spacially determined the sampling rate is spacially dependent and time and velocity independent. According, the Nyquist frequency is independent of detector velocity in the present invention.

A further advantage of the present invention is a reduction in vibrational interference. Vibration is reduced in a number of ways, such as a continuous speed traverse motor, gradual traverse speed changes, and a flexible drive to name a few.

Still another advantage of the present invention is the smooth cable handling operation. The cable handling allows flexible interconnection with electric components mounted on the carriages without cable tangling and vibrational or other interference with the carriage travel.

BRIEF DESCRIPTION OF THE DRAWINGS

The invention may take physical form in certain parts and arrangements of parts, a preferred embodiment of which will be discussed in detail in this specification and illustrated in the accompanying drawing.

DESCRIPTION OF THE PREFERRED EMBODIMENT

Figure 1:
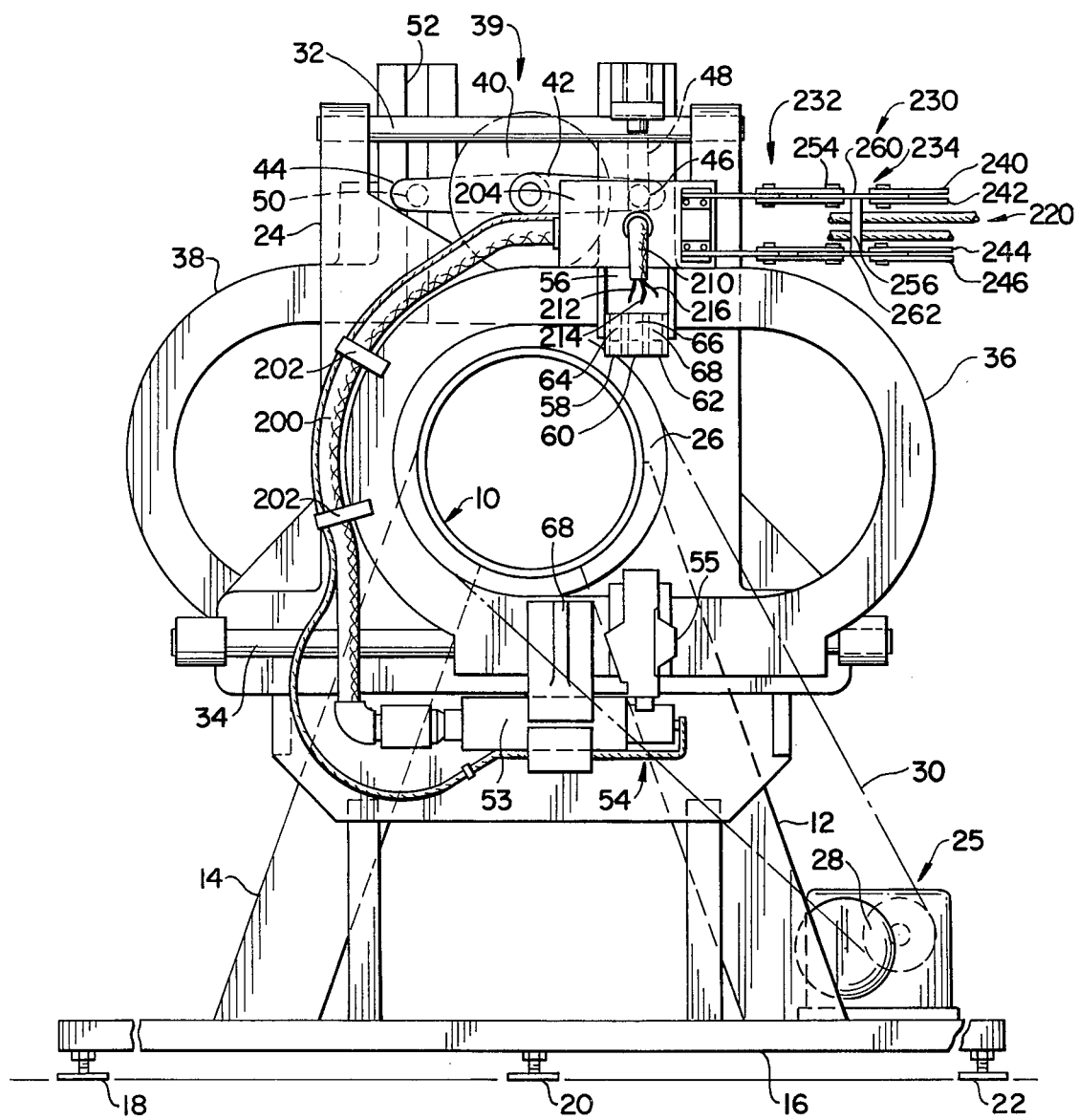
FIG. 1 is a front view of a traverse and rotate system in accordance with the present invention.

Referring now to the drawings wherein the showings are for the purpose of illustrating the preferred embodiment of the invention only and not for the purposes of limiting same.

Figure 2:
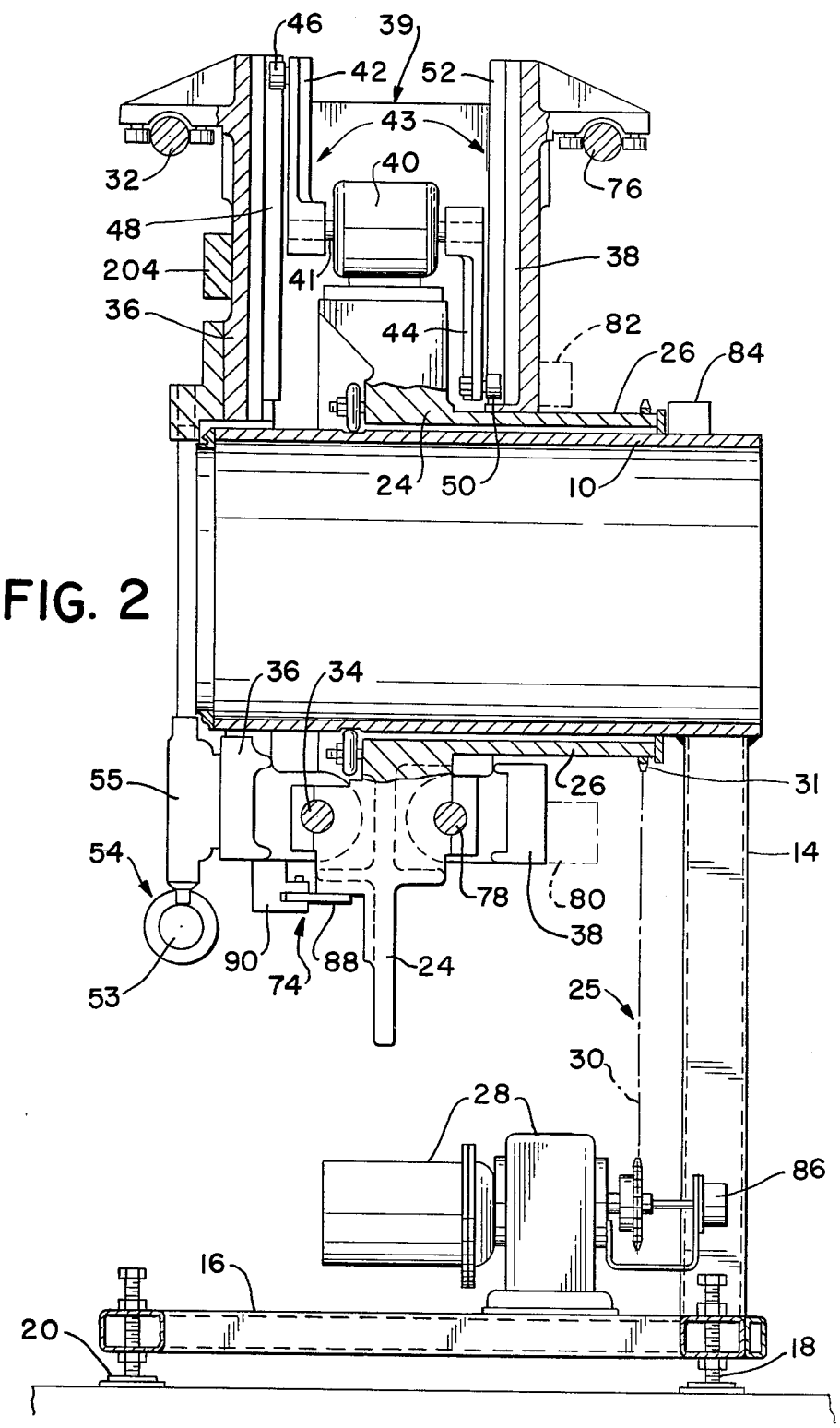
FIG. 2 is a side sectional view of a traverse and rotate system in accordance with the present invention with the radiation source and detector carriage and counter balance carriages centered.

FIGS. 1 and 2 show a traverse and rotate scanner 10 built in accordance with the present invention. At the center of the scanner is a stationary cylinder 10 in which the object to be scanned is positioned. In the preferred embodiment, the cylinder 10 would be about ten inches in diameter, or sufficient to encompass the region to be examined, i.e. scan circle. The cylinder may be sized to receive the head of a patient for brain scanning, although other sizes may be used. Supporting and attached to the stationary cylinder 10 are a pair of legs 12 and 14 which mount the cylinder and other apparatus on a large base 16. Adjustable feet, three of which are illustrated at 18, 20 and 22 operatively attached to the base 16, are used for leveling.

Mounted for rotation about the cylinder 10 is a frame or plate 24. The frame 24 is integral with cylinder 26 through which it is rotatably mounted upon cylinder 10. Means 25 for incrementally rotating the frame 24 and cylinder 26 includes a rotational drive comprising a motor 28 connected with a gear box, a sprocket and a flexible drive chain 30. Chain 30 in turn engages cylinder 26 by being pinned to it or, alternately, by a ring 31 of sprocket teeth circumscribing cylinder 26. As drive motor 28 is rotated incrementally, the frame 24 is caused to assume different angular orientations incrementally about the object in cylinder 10. The rotational drive is described in greater detail below. Mounted on the front of frame 24 are a pair of upper and lower bars 32 and 34, upon which a means for supporting a radiation source and radiation detectors is slidably mounted. In the preferred embodiment this supporting means takes the form of a carriage 36. Another pair of bars 76 and 78 are similarly mounted on the back of frame 24 to carry counter balance means such as a carriage assembly 38.

A means 39 for traversing the carriage includes a rotary power source such as a torque motor 40 mounted on a platform on frame 24 and a nonlinear drive means 43. The nonlinear drive means includes a central shaft 41 which in this embodiment is integral with the armature of motor 40 on the opposite ends of which are mounted lever arm means in the form of a pair of lever arms 42 and 44. Between the lever arm 42 and the carriage 36 is an engaging means for slidably coupling the lever arm and carriage for transferring movement from the arm to the carriage. In the preferred embodiment this engaging means includes a wheel or follower 46 mounted on the arm 42 and a track 48 on carriage 36 in which the follower rides. Similarly, there is another engaging means between arm 44 and counter balancing carriage 38. This engaging means includes follower 50 and a track 52 on the counter balance carriage 38 in which the follower rides. It can be seen that as power source 40 rotates, the followers 46 and 50 pull and push the carriages 36 and 38 back and forth along bars 32, 34, and 76, 78 respectively. This illustrated drive assembly is known as a Scotch yoke which it may be noted causes the carriages to oscillate back and forth with substantially simple harmonic motion when driven by a constant speed power source. Other drives which cause other forms of smoothly changing back and forth motion are equally applicable. Mounted on carriage 36 is a source of radiation 54 composed of an X-ray tube 53 and a collimator and shutter assembly 55, a radiation detection means 56, the housings for mounting the detection means and normal electrical connections. In the preferred embodiment, the source of radiation is collimated by assembly 55 to form three finger-like beams of radiation angularly displaced from each other on two degree centers. Other number of beams and spacings, however, may be chosen. In the detection means 56, opposite each of the three diverging pencil-like beams of radiation are three scintillation crystals 58, 60 and 62 which are connected to the three photoelectric transducers such as photomultiplier tubes 64, 66 and 68. Thus, as the carriage 36 traverses the object positioned in cylinder 10, the detection means 56 will produce three sets of attenuation data. For example, data may be obtained from a parallel sets of beams at zero degrees, two degrees, and four degrees relative to vertical during the first traverse.

FIG. 2 is a side view of the assembly of FIG. 1 with the carriages 36 and 38 centered. As shown more clearly in this view, counter weight carriage 38 may have added weights 80 and/or 82 to give carriage 38 the the same mass as carriage 36 with the radiation source and detection mechanisms attached. Rather than being add on weights as illustrated in FIG. 2 in phantom, the weights may be lead inserts or merely thicker construction of the counter balance carriage assembly.

The incremental rotation means 25 is also illustrated more clearly in FIG. 2. In the preferred embodiment, the cylinder 26 is rotated incrementally in three degree steps, although other increments are within the scope of the invention. When an odd number of radiation beams N is used and the beams are 2° apart, then rotating the cylinder 26 in increments of N degrees produces data sets representing traverses at 1° rotational increments and after 60 traverses enables collection of 180 unique sets. Incremental rotation may be achieved by using a displacement measuring means 84, for measuring the rotation of cylinder 26 relative to cylinder 10. Alternately, a means 86 which measures the angular rotation of the drive shaft for driving chain 30 could also be used. As a third alternative, a mechanism for measuring the linear displacement for a number of links of chain 30 could be used. A specific incremental measuring means is the model LM-14.0-500-IX 4 manufactured by Disc Instruments of Costa Mesa, California. The placement of the rotation drive 28 remote from the area of examination and the interconnection with a flexible drive 30, is effective for isolating vibrations in the rotation drive from the rest of the structure. Other linkages between motor 28 and cylinder 26 may, however, be used.

A spacial displacement detection means 74 is mounted between carriage 36 and frame 24. This means measures the spacial displacement of carriage 36 relative to frame 24 as it slides along bars 32 and 34 during a traverse movement. The detector means 74, includes a spacial gradient or increment means 88 bearing spacial increment marking extending along frames 24 and reading means 90 for reading the incremental markings on 88. A specific spacial displacement detector which may be used is model LM-14.0-500-IX 4 manufactured by Disc Instruments of Costa Mesa, California.

In operation, the patient is positioned such that the planar slice of the body to be examined is positioned between the radiation source 54 and detection means 56. Having positioned the patient, the tomographic scan may be commenced.

The carriage 36 starts displaced to one side such as in FIG. 1. The motor means starts accelerating carriage 36 to the left, subjecting the planar slice of the body to radiation. At spacially regular intervals, for example every millimeter, displacement detector 74 causes the photomultiplier tubes 64–68 to be sampled. Upon decelerating to a momentary stop at the extreme left position, the photomultiplier tubes will have produced three sets of scan data—one set representing the attenuation along a series of vertical parallel lines, a second set representing the attenuation along a series of parallel lines displaced 2° from vertical, and a third set representing attenuation data along parallel lines displaced 4° from vertical.

The incremental rotation means 25 is actuated causing frame 24 and carriage 36 to be rotated by 3°. Because bars 32 and 34 have been rotated 3° from horizontal, on the return traverse, attenuation data along parallel lines displaced 3°, 5° and 7° from vertical will be collected. This traverse and rotate operation is repeated until at least 180 sets of attenuation data are collected. In the preferred embodiment this takes about two minutes.

It will be observed that counter balance carriage 38 is caused to traverse in the opposite direction from carriage 36. Because at any given instant the velocity of these two carriages of the same mass is equal but opposite, the net momentum is substantially zero.

It will further be observed that when motor 40 rotates at a constant speed, the Scotch yoke causes the carriage to traverse back and forth with a varying velocity. Because the velocity of the traverse is varying and the data is sampled at spacially regular intervals, the data samplings are time independent. Thus, the samplings are made at temporally varient but spacially constant intervals.

Figure 3:
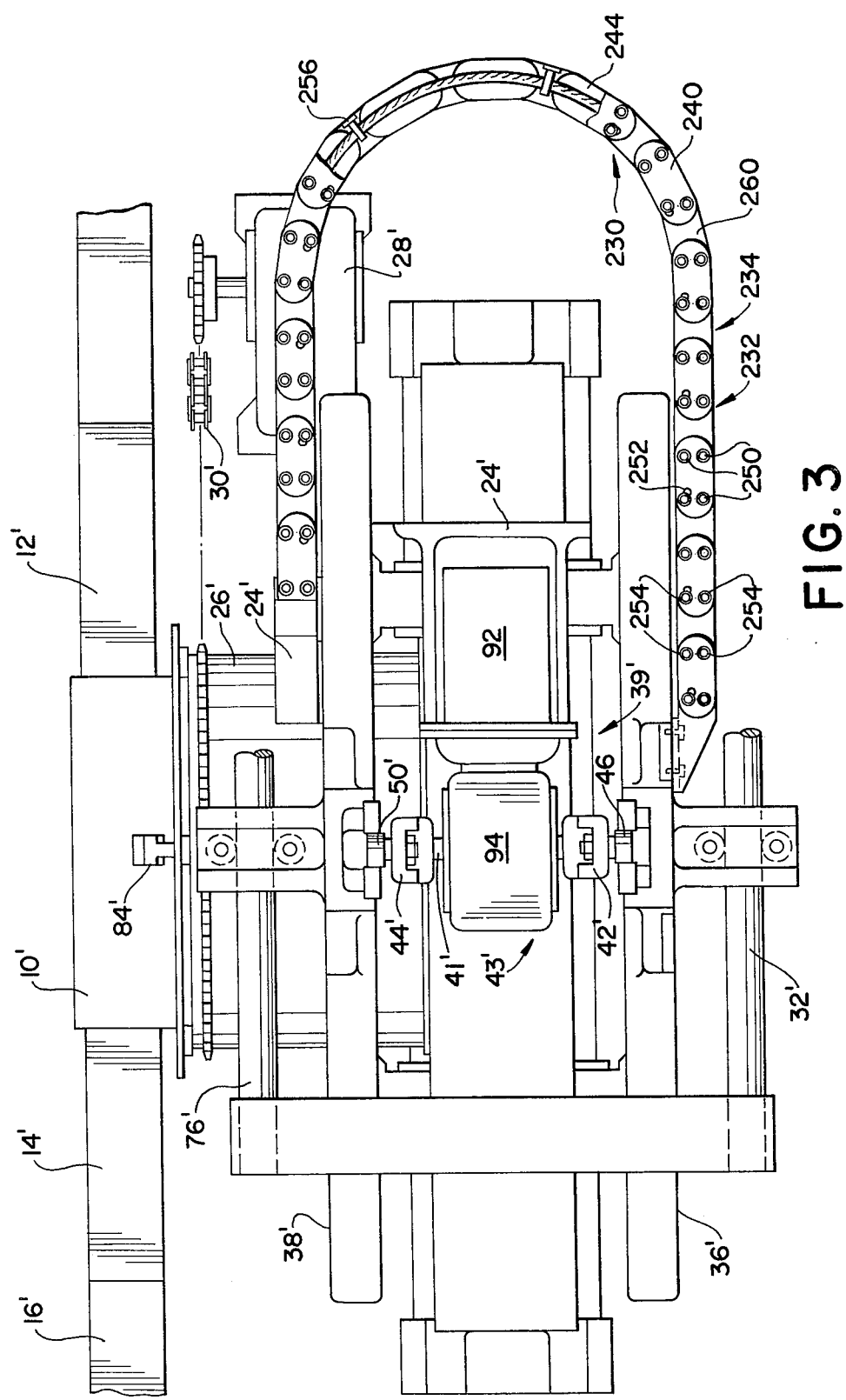
FIG. 3 is a PLAN view of an alternate embodiment of a traverse and rotate system in accordance with the present invention with a gear motor power supply.

FIG. 3 is a top view of an alternate embodiment of a traverse and rotate scanner in accord with the present invention for illustrating an alternate means for traversing the carriage. Common elements with the embodiment of FIGS. 1 and 2 are marked with like reference numerals followed by a prime ('). The power source, a gear motor 92, is mounted on carriage supporting frame 24' and has its output connected to a gear box 94. The nonlinear drive means includes gear box 94 and central shaft 41' to which arms 42' and 44' for traversing carriages 36' and 38'. In this embodiment the central shaft is integral with output shaft of gear box 94. In the preferred embodiment, motor 92 is run at substantially constant speeds for efficient use of space, time and funds and to minimize vibration. However, as indicated above because the radiation source and detectors do not need to traverse at a linear speed, motor 92 may be allowed or caused to operate at a constant or fluctuating angular velocity. Similarly, gear box 94 may be a straight forward mechanical linkage which causes arms 44' and 42' to rotate at a constant angular velocity. Again, because the carriage need not, and in the preferred embodiment does not, traverse at a constant linear speed, gear box 94 may be most any linear or nonlinear linkage. For example, a gear box may be chosen with nonlinear gearing which causes the radiation source and detector to traverse the object being examined at a substantially linear constant speed or any one of a number of fluctuating traverse speeds. Gear box 94 may also adjust the angular velocity of arms 42' and 44' so that the radiation source and detectors traverse with simple harmonic motion or with fluctuations of speed. Thus, in this embodiment gear box 94 can be chosen to cause the nonlinear drive means to traverse the source and detectors relative to the object at a constant speed as in the prior art scanners or at a nonconstant speed.

Figure 4:
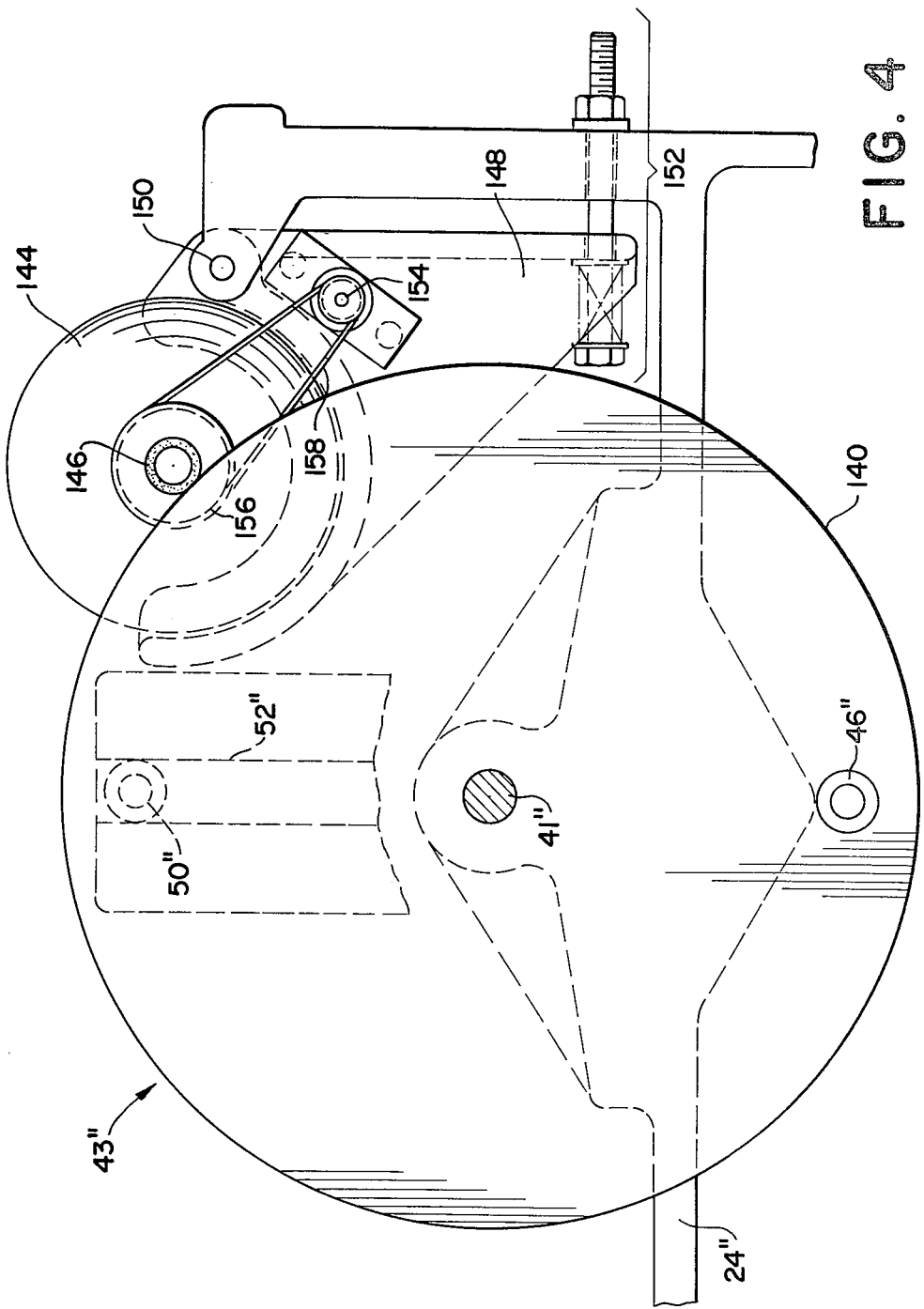
FIG. 4 is a front elevational view of another alternate embodiment of a traverse drive system in accordance with the present invention.

FIG. 4 shows another alternate embodiment of the means for traversing the carriages (like elements marked with a double prime). In this embodiment the nonlinear drive means includes a flywheel 140 which is mounted on central shaft 41" journalled in frame 24". The engagement means includes a pair of rollers or followers 46" and 50" interconnected with shaft 41" at a 180° offset and tracks 48" and 52" on the carriages in which the followers ride. In this drive system, one or more flywheels rotate with shaft 41" and lever arm means connect the shaft with the followers. Each of the followers 46" and 50" may be mounted on an individual lever arm, or each may be mounted on a flywheel making the lever arm means an integral part of the flywheel, or one may be mounted on the flywheel and one on an individual lever arm. Further, flywheel 140 may either be mounted on the shaft or connected to it by gears or belts.

The flywheel 140 is driven by the power source such as an electric motor 144 with the motor having a surface 146 on its armature shaft for engaging and driving flywheel 140. The motor is mounted on a plate 148 which is pivoted at pivot 150. A positioning means 152 adjusts the degree of physical engagement or pressure between shaft surface 146 and flywheel 140.

An encoder or tachometer 154 indirectly monitors the speed of the shaft 41" and flywheel 140 by monitoring the speed of motor 144 to which it is connected by a pulley 156 and belt 158. The tachometer is used to control the speed of motor 144, holding it, the flywheel, and shaft 41" to a constant speed. The constant speed from the inertia of the flywheel and the constant monitoring of motor 144's speed, causes followers 46" and 50" to traverse the carriages very smoothly. This smoothness reduces vibrations and thereby does not impair spacial resolution.

In operation these alternate embodiments function essentially the same as the embodiment of FIGS. 1 and 2, although these alternate embodiments may rotate shaft 41 with a smoother more constant angular velocity than the embodiment of FIGS. 1 and 2 or with nonconstant angular velocities. The sampling of the radiation detectors, as explained above, being dependent only on spacial position and independent of time or traverse velocity, the resultant attenuation data sets will be the same as in the embodiment of FIGS. 1 and 2.

The cable system includes an electric cable 200 for supplying power to X-ray tube 53 and for controlling the shutter and collimator of assembly 55. A series of clips 202 anchors cable 200 to carriage 36. The end of cable 200 opposite the radiation source is connected to a junction box or electrical housing 204.

A second cable 210 having at least leads 212, 214 and 216 connects photoelectric transducers 64, 66 and 68 respectively with electrical junction box 204. Also connected with the junction box is a combined cable means 220 which cables the leads of cables 200 and 210 into a single larger cable. Alternately a plurality of cables may be used.

A flexible cable support means 230 supports cable means 220 between moveable carriage 36 and frame 24.

Cable support means 230 is flexible in the plane which is horizontal in FIG. 1 and rigid in the plane which is vertical in FIG. 1. The cable support means follows a generally arcuate path from the carriage to the frame. As the carriage traverses the cable support means flexes such that the arcuate path segment is shifted in space.

In the preferred embodiment, the cable support means is made up of a series of links—alternating main links 232 and connecting links 234. The main links each have a generally rectangular top plate or preferably pair of plates 240 and 242; a generally rectangular bottom plate or preferably pair of plates 244 and 246. Each of the plates is drilled with three round holes 250 and one elongate hole 252 to receive connecting pins 254.

The top and bottom plates are maintained in a spaced relationship by spacing means 256 such as strips connecting the plates or shoulders on pins 252, which engage the top and bottom plates. The spacing means further serve to guide cable means 220 and hold it within the support.

The connecting links are made up of a pair of plates 260 and 262 each of which have four round holes for receiving pins 254. The elongate holes 252 allow the main links to pivot relative to the connecting links but sliding contact of the main and connecting links prohibit movement out of the plane of the link plates. This allows only single planar flexing of support means, i.e. two degrees of freedom.

Support means 230 arcs around to the rear of frame 24 where cable means 220 is attached to the frame. Any convenient means may be used for connecting the cable means from the frame to the power supply, processor and other electrical equipment.

Figure 5:
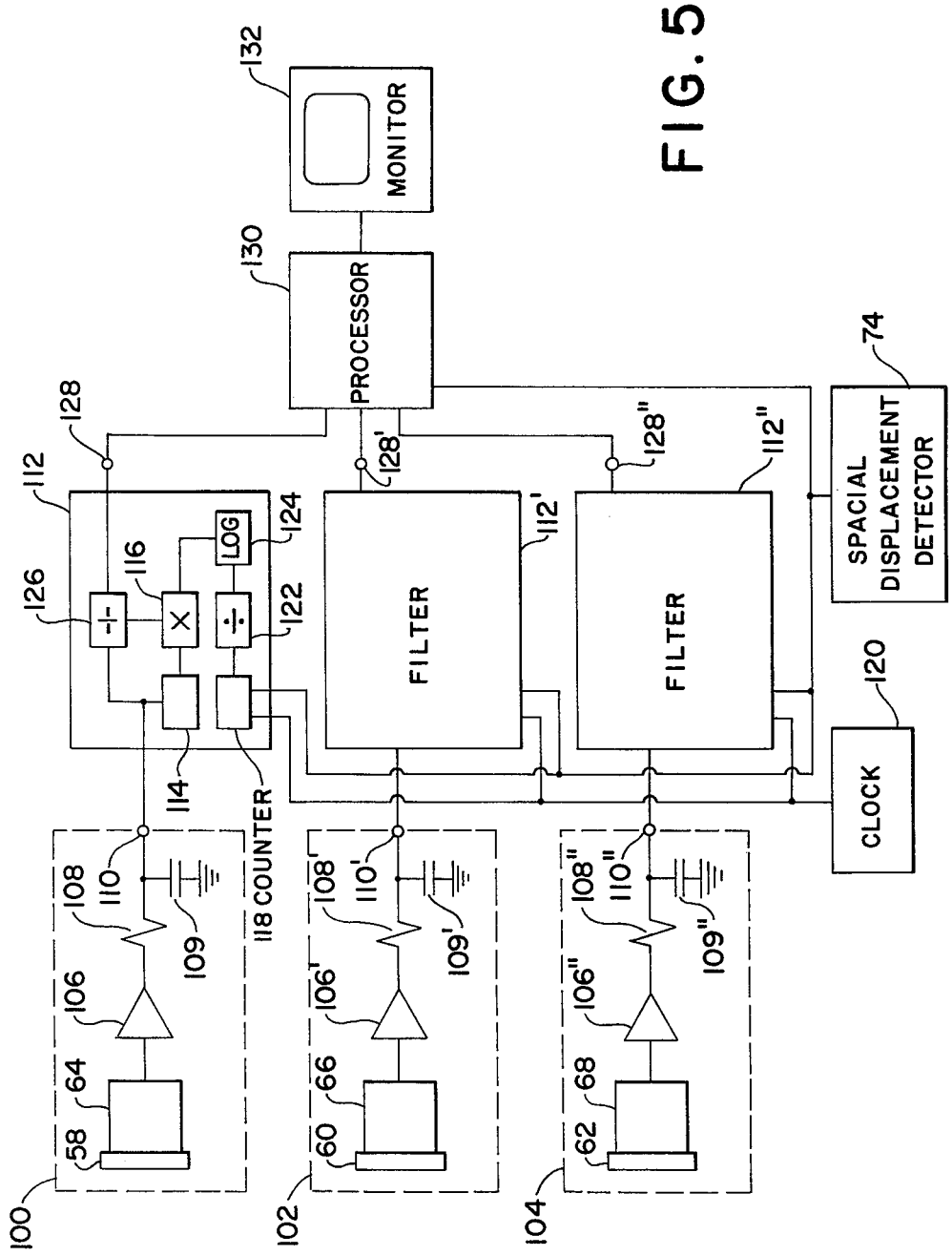
FIG. 5 is a diagrammatic illustration of a signal handling system in accordance with the present invention.

In FIG. 5 a diagram of the attenuation data receiving and handling system is shown. There are three attenuation data receiving circuits 100, 102 and 104 in the preferred embodiment—one corresponding to each of the combination scintillation crystal and photomultiplier tube detectors. Accordingly, the exact number of data receiving circuits will vary with the detection means chosen.

Looking to data receiving circuit 100 as typical, scintillation crystal 62, which may be a thallium doped sodium iodide crystal receives radiation and produces photoluminessence in proportion to the amount of radiation impinging thereupon. Photomultiplier tube 68 transforms the intensity of photoluminessence into a current representative of the intensity. The output current of the photomultiplier tube is amplified by log amp 106. The output of the log amp is connected through a resistive element 108 to an output 110. Further, there is a capacitive element 109 connecting the output to ground. As the radiation source and the radiation detector traverse across the object examined, the amount of radiation striking the scintillation crystal will fluctuate with the degree of attenuation along the path through the body. As the amount of radiation fluctuates so does the signal at output 110.

Each of the data receiving circuits has an RC time constant. One way of expressing the RC time constant is as the time need for the signal at output 110 to decay to $e^{-1}$ if the radiation impinging on the crystal were instantaneously stopped. In the preferred embodiment this time is about two milliseconds. It is apparent that if the output 110 were sampled twice in a time period shorter than the time constant, then the second sampled output would be composed of two components. One of the components is the signal indicative of the actual amount of radiation currently detected and the other component is the carried over signal from the previous sampling which had not yet decayed to zero. This carry over then is a source of error in the second sampling.

There are at least two solutions for the carry over error. One solution is to operate the system slowly enough that the time between samplings at the maximum transverse speed is as great or greater than the time constant. Another solution is to correct each sampled signal by the amount of the carried over component.

The first solution, it has been found is satisfactory under some acceptable operating conditions. The maximum speed may easily be determined by speeding up the traverse speed until there is a degradation in resolution. For example, if the spacial sampling interval is 1 millimeter, the maximum speed about 12 inches per second, and the RC time constant is two milliseconds, then no correction has been found to be needed.

The other solution is to subtract the carried over component from the output signal. The carried over component may be approximated multiplying the previous signal by the filter valve $$-e^{-\frac{\Delta x}{\tau}}$$

where $\Delta x$ is the constant spacial increments between sampling and $\tau$ is spacial equivalent of the RC time constant. $\tau$ is determined by the formula $$\tau = \frac{t_{RC} \cdot \Delta x}{t_{\Delta x}}$$

where $T_{RC}$ is the known RC time constant and $t_{\Delta x}$ is the elapsed time since the preceding sampling. As expressed above as the first solution, when $t_{\Delta x}$ is large compared to $t_{RC} \cdot \Delta x$ then the correction becomes negligable.

To perform this correction an extrapolation filter means 112 is used. Filter means 112 may be a suitable microcomputer or suitably programmed digital computer. The computer has a memory 114 to store a first output signal from output 110. When the computer then reads a second output signal, it places the second signal in memory 114 and moves the first signal to multiplier 116. The time interval between the first and second sampling is determined by a counter 118, which is connected to a clock 120 and spacial increment sensor 74. A divider 122 connected with counter 118 determines $\tau$ by dividing the product of the RC time constant and $\Delta x$, a constant for the system, by the time from counter 118. A circuit 124 connected with divider 122 calculates the filter value $$-e^{-\frac{\Delta x}{\tau}}.$$

Multiplier 116 multiplies the first output signal by the filter value to produce a correction factor. An adder 126 combines the second output signal with the correction factor. An analogous procedure is followed for each sampling in each traverse.

It is apparent that if the traverse speed is slow, the output signal at output 110 is essentially the same as the signal at output 128. This for lower traverse speeds, the filter means 112 is superfluous.

Connected to the outputs of each of the filter means 112, 112', and 112" if used and if not used to outputs 110, 110', and 110" is a processor 130. The processing for transforming data from a traverse and rotate scanner into a visual representation of the radiation attenuation across a planar section of an examined object is well-known in the art. An example of a processing means which may be used is a programmable digital computer programmed to implement the algorithms set forth in "The Fourier Reconstruction of the Head Section" L. A. Shepp and B. F. Logan, IEEE Transactions on Nuclear Science, June, 1974. Alternately the algorithems set for in "Optimum Reconstruction of a Function from Its Projections" Logan and Shepp, Duke Mathematics Journal, Vol. 42, Vol. 4, December, 1975 can be implemented. As a third alternative the implementation shown in U.S. Pat. No. 3,924,129 is usable.

The processor is connected with the spacial displacement detector 74 which cues the processor to sample the outputs 128 or 110. Further, the processor is connected with a T.V. monitor 132 on which the visual representation produced by the processor is displayed.

It will be appreciated that a single computer can be programmed to perform the function of processor 130 and of a plurality of filter means 112.

The above illustrated preferred embodiment is by way of example an explanation only and is not intended to limit the invention to any of the specific details set forth above beyond limitations and restrictions of the claims which follow.

We claim:

1. Apparatus for examining an object with penetrating radiation comprising:
   a frame means;
   a carriage movably mounted on said frame means and holding a source of radiation and radiaton detection means;
   said source of radiation and said detection means disposed on opposite sides of the examined object;
   means for traversing said carriage along said frame means at a nonconstant speed as said source of radiation and said detection means traverse past the examined object;
   said traversing means including a torque motor which supplies motive force to drive the carriage, a flywheel operatively connected with said torque motor, a lever arm means operatively connected with said flywheel for rotation at a generally constant speed, and engaging means operatively connected between said carriage and said lever arm means for transferring movement of said lever arm means to said carriage; and
   incremental rotating means operatively connected with said frame means for rotating said carriage an incremental angular distance after a traverse.

2. The apparatus as set forth in claim 1 wherein said torque motor rotates the flywheel at a substantially constant angular velocity.

3. The apparatus as set forth in claim 1 wherein said lever arm is an integral part of said flywheel.

4. Apparatus for examining an object with penetrating radiation comprising:
   a frame means;
   a carriage movably mounted on said frame means and holding a source of radiation and radiation detection means;
   said source of radiation and said detection means disposed on opposite sides of the examined object;
   means for traversing said carriage along said frame means at a nonconstant speed as said source of radiation and said detection means traverse past the examined object;
   said traversing means including a power source for supplying motive force to drive the carriage, a flywheel operatively connected with said power source, a lever arm means operatively connected with said flywheel for rotation at a generally constant speed, encoder means for monitoring the speed of said lever arm means and for controlling said power source to maintain the speed of said lever arm means substantially constant, and engaging means operatively connected between said carriage and said lever arm means for transferring movement of said lever arm means to said carriage; and
   incremental rotating means operatively connected with said frame means for rotating said carriage an incremental angular distance after a traverse.

5. The apparatus as set forth in claim 4 wherein said lever arm means is an integral part of said flywheel.

6. Apparatus for examining an object with penetrating radiation comprising:
   a frame means;
   a carriage moveably mounted on said frame means and holding a source of radiation and radiation detection means;
   said source of radiation and said detection means disposed on opposite sides of the examined object;
   means for traversing said carriage along said frame means so that said source of radiation and said detection means traverse past the examined object;
   incremental rotating means operatively connected with said frame means for rotating said carriage an incremental angular distance after a traverse; and
   cable support means for supporting at least electrical connections for the source of radiation and the radiation detection means, said cable support means comprising a first end connected with said frame, a second end connected with the carriage, and a self-supporting intermediate section disposed between the first and second ends, said intermediate section disposed in a generally planar, substantially U-shaped path, said intermediate section comprising a plurality of pivotally connected links which are unsupported by the frame or the carriage, said cable support means being flexible only in the plane of the U-shaped path.

7. The apparatus as set forth in claim 6 wherein the plane of the U-shaped path is substantially parallel to the traversing direction and substantially normal to a radiation path between the source and the detection means.

8. The apparatus as set forth in claim 6 wherein said cable support means has at most two degrees of freedom.

9. Apparatus for examining an object with penetrating radiation comprising:
   a frame means;
   a carriage movably mounted on said frame means and holding a source of radiation and radiation detection means;
   said source of radiation and said detection means disposed on opposite side of the examined object; and
   means for traversing said carriage along said frame means at a nonconstant speed as said source of radiation and said detection means traverse past the examined object, said traversing means comprising a power source operatively connected with a nonlinear drive means for supplying the motive force to drive the carriage, a shaft operatively connected with said power source, and a lever arm means operatively connected to said shaft; and engaging means operatively connected between said carriage and said lever arm means for transferring movement of said lever arm means to said carriage, said engaging means comprising a slot operatively connected to said carriage and a follower operatively connected to said lever arm means and disposed to slidingly engage said slot, whereby rotary motion from the power source rotates the shaft which rotates the lever arm means which causes the carriage to traverse back and forth on the frame means; and incremental rotating means operatively connected with said frame means for rotating said carriage an incremental angular distance after a traverse.

10. The apparatus as set forth in claim 9 wherein said nonconstant speeds are each substantially simple harmonic motion.

11. The apparatus as set forth in claim 9 wherein said power source is connected to said shaft by a gear box.

12. The apparatus as set forth in claim 9 wherein said slot is linear.

13. The apparatus as set forth in claim 12 wherein said linear slot is generally normal to the direction of traverse whereby the carriage is traversed with generally simple harmonic motion.

14. The apparatus as set forth in claim 9 further comprising correction means for correcting errors in a sampled output from the detection means which sampled output is sampled a short temporal interval after a preceding output output is sampled from the detection means, said correction means being operatively connected with said detection means; and processing means for processing corrected sampled outputs into an image representing radiation absorption by the object, said processing means being operatively connected with said correction means.

15. The apparatus as set forth in claim 14 wherein said correction means comprises means for storing the preceding output, means for determining the temporal interval between the sampling of the preceding output and the sampling of the preceding output and the sampled output, means for reducing the preceding output as a logarithmic function of the temporal interval to produce a correction factor, and means for combining the correction factor with the sampled output.

16. The apparatus as set forth in claim 9 wherein said power source rotates said shaft with substantially constant angular velocity.

17. The apparatus as set forth in claim 16 wherein said power source is a torque motor having an armature integrally connected with said shaft.

18. The apparatus as set forth in claim 16 wherein said traversing means further includes a flywheel operatively connected with said shaft whereby the flywheel assists in maintaining the rotation speed of the shaft generally constant.

19. Apparatus for examining an object with penetrating radiation comprising:
a frame means,
a carriage moveably mounted on said frame means and holding a source of radiation and radiation detection means;
counter balance means moveably mounted on said frame for counterbalancing said carriage;
said source of radiation and said detection means disposed on opposite sides of the examined object; and
means for traversing said carriage along said frame means at a nonconstant speed as said source of radiation and said detection means traverse past the examined object, said traversing means including a substantially constant speed motor mounted on said frame, said motor including an armature shaft, a first lever arm operatively connected with said armature shaft for rotation therewith, a first engaging means operatively connected between said carriage and said lever arm for transferring movement from said lever arm means to said carriage, and
a second lever arm operatively connected to said armature shaft, a second engaging means operatively connected to said lever arm means, and said second engaging means operatively connected to said counterbalance means; and
incremental rotating means operatively connected with said frame means for rotating said carriage an incremental angular distance after a traverse.

20. The apparatus as set forth in claim 19 wherein said first lever arm means and said second lever arm means are a pair of lever arms angularly displaced by 180 degrees relative to each other whereby said carriage and said counterbalance means traverse said object 180 degrees out of phase.

21. The apparatus as set forth in claim 19 wherein said incremental rotating means includes a rotational motor means and a flexible drive means for operatively connecting the rotational motor means with to said frame means whereby the flexible drive means vibrationally insulates the carriage from the rotational motor means.

22. The apparatus as set forth in claim 19 further including means for measuring spacial displacement of said carriage relative to said object and processing means connected with said displacement measuring means and said radiation detection means for sampling the radiation detection means at intervals that are spacially regular and temporally variant.

23. The apparatus as set forth in claim 22 further including display means connected to said processing means and wherein said processing means transforms the sampling of the radiation detection means into a representation of a planar region of said object for display on said display means.

24. The apparatus as set forth in claim 19 further including a cable support means for supporting a cable for electrical connections to at least the source of radiation connected between said carriage and said frame, said cable support means being arranged in a generally arcuate planar path and being flexible only within the plane of the path whereby the cable support means is constrained to motion in a single plane.

25. The apparatus as set forth in claim 24 wherein said path has a substantially constant length.

26. The apparatus as set forth in claim 19 further comprising correction means for correcting errors in a sampled output from the detection means which sampled output is sampled a short tempral interval after a preceding output is sampled from the detection means, said correction means being operatively connected with said detection means; and processing means for processing corrected sampled outputs into an image representing radiation absorption by the object, said processing means being operatively connected with said correction means.

27. The apparatus as set forth in claim 26 wherein said correction means comprises means for storing the preceding output, means for determining the temporal interval between the sampling of the preceding output and the sampled output, means for reducing the preceding output as a logarithmic function of the temporal interval to produce a correction factor, and means for combining the correction factor with the sampled output.

28. Apparatus for tomographically examining the body of the patient in order to produce an image of the variation of absorption coefficient with respect to penetrating radiation over a planar region of said body comprising:
 positioning means for defining a patient position;
 frame means rotatably mounted on said positioning means;
 a carriage mounted on said frame means for reciprocating traverse movement relative to said frame means;
 a second carriage mounted on said frame means for reciprocating motion 180 degrees out of phase with said first carriage means;
 traversing means mounted on said frame means for causing said first and said second carriage means to undergo linear traversing movement;
 a source of radiation and a radiation detecting means mounted on said carriage and disposed to pass on opposite sides of said patient position when said carriage is traversed with respect to said frame means;
 processing means connected to said radiation detecting means for sampling the output of said radiation detecting means and for producing an image representing the variation of absorption over the planar region of the patient;
 rotating means for rotating said frame means relative to said positioning means including a rotational motor means substantially vibrationally isolated from said frame means and a flexible drive means connecting said motor means and said frame means, whereby vibrations from said rotational motor means are isolated from said frame means by said flexible drive.

29. The apparatus of claim 28 wherein said traversing means includes a Scotch yoke for moving said radiation source with generally simple harmonic motion.

30. The apparatus as set forth in claim 28 wherein said linear traversing movement is a nonconstant velocity as said source of radiation moves past said positioning means.

31. The apparatus set forth in claim 28 further including a first sprocket operatively connected to said rotational motor means to be rotated thereby, a second sprocket operatively connected to said frame means and wherein said flexible drive means is a chain mounted between said first and second sprockets.

32. The apparatus as set forth in claim 28 further including control means for controlling incrementally the rotation of the frame means by the rotational motor means comprising means mounted on said positioning means for measuring the angular displacement of said frame means relative to said position means and for stopping rotation of said rotational motor means after a preselected degree of rotation between said positioning means and said frame means.

33. The apparatus as set forth in claim 28 further including a cable support means for supporting at least a cable for carrying electrical connections at least to the source of radiation said cable support means connected between said carriage and said frame.

34. The apparatus as set forth in claim 33 wherein said cable support means includes a series of links having no more than two degrees of freedom.

35. Apparatus for examining an object with penetrating radiation comprising:
 a frame means;
 a carriage moveably mounted on said frame means and holding a source of radiation and radiation detection means;
 means for traversing said carriage along said frame means at a nonconstant speed as said source of radiation and said detection means traverse past the examined object;
 incremental rotating means operatively connected with said frame means for rotating said carriage an incremental angular distance after a traverse;
 said source of radiation and said detection means disposed on opposite sides of the examined object, said detection means comprising a receiving means for receiving radiation and producing an output which is indicative of the intensity of the received radiation whereby the output fluctuates with fluctuations in the intensity of received radiation as the carriage traverses along the frame;
 correction means for correcting errors in a presently sampled output sampled a short temporal interval after sampling a preceding sampled output, the correction means being operatively connected with the detection means, said correction means comprising means for storing the preceding sampled output, means determining the temporal interval since the preceding sampled output was sampled, means for reducing the stored preceding sampled output as a logarithmic function of the temporal interval to produce a correction factor, and means for combining the correction factor with the presently sampled output to produce a corrected output; and
 processing means for processing corrected output into an image representing the radiation absorption of the object, said processing means operatively connected with the correction means.

36. Apparatus for examining an object with penetrating radiation comprising:
 a frame means,
 a carriage moveably mounted on said frame means and holding a source of radiation and radiation detection means;
 said source of radiation and said detection means disposed on opposite sides of the examined object, said source of radiation including collimator means for collimating the radiation into N pencil beams of radiation each displaced by 2 degrees where N is an odd number; said radiation detection means includes N radiation detectors each positioned to receive one of said N pencil beams of radiation;
 means for traversing said carriage along said frame means at a nonconstant speed as said source of radiation and said detection means traverse past the examined object; and
 incremental rotating means operatively connected with said frame means for rotating said carriage in increments of N degrees.

* * * * *

UNITED STATES PATENT AND TRADEMARK OFFICE
CERTIFICATE OF CORRECTION

PATENT NO. : 4,253,027

DATED : February 24, 1981

INVENTOR(S) : Samuel K. Taylor et al

It is certified that error appears in the above—identified patent and that said Letters Patent is hereby corrected as shown below:

Column 9, line 36, second occurrence "radiaton" should read --radiation--. Column 11, line 38, delete one occurrence of the word "output". Column 12, line 4, " counter balance" should read --counterbalance--. Column 12, line 67, "tempral" should read --temporal--.

Signed and Sealed this

Fifth Day of January 1982

[SEAL]

Attest:

Attesting Officer

GERALD J. MOSSINGHOFF

Commissioner of Patents and Trademarks